United States Patent [19]

Ceska

[11] 4,066,509

[45] Jan. 3, 1978

[54] DETECTION OF HYDROLYZING ENZYMES

[75] Inventor: Miroslav Ceska, Uppsala, Sweden

[73] Assignee: Boehringer Mannheim GmbH, Mannheim, Germany

[21] Appl. No.: 440,944

[22] Filed: Feb. 8, 1974

Related U.S. Application Data

[63] Continuation of Ser. No. 178,671, Sept. 3, 1971, abandoned.

[30] Foreign Application Priority Data

Sept. 11, 1970 Sweden ............................ 12379/70

[51] Int. Cl.² ............................................. G01N 31/14
[52] U.S. Cl. ................................ 195/103.5 R; 195/99
[58] Field of Search ......................... 195/103.5 R, 99; 23/253 TP, 230 B

[56] References Cited

U.S. PATENT DOCUMENTS 3,416,998  12/1968  Streitfeld .................. 195/103.5 R
3,676,303  7/1972  Ingelman et al. .......... 195/103.5 R

OTHER PUBLICATIONS

Sbarra, et al., A Plate Assay for Elastase Nature, vol. 188, 1960 (pp. 322–323).
Hall; D. A., The Identification and Estimation of Elastase in Serum and Plasma, Biochem. J., vol. 101, 1966, (pp. 29–36).
Merkel; J. R., Method for Detecting and Isolating Proteolytic Marine Bacteria, Journal of Bacteriology, vol. 89, No. 3, 1965 (pp. 903–904).
Lanyi; et al., Fluorescent Method for The Detection of Excreted Ribonuclease Around Bacterial Colonies Journal of Bacteriology, vol. 92, No. 5, 1966 (pp. 1469–1472).

*Primary Examiner*—David M. Naff
*Attorney, Agent, or Firm*—Burgess, Dinklage & Sprung

[57] ABSTRACT

The activity, or concentration, of a hydrolyzing enzyme, e.g., an endo-enzyme, is determined by providing a detection layer comprising a carrier matrix and a water-insoluble substrate dispersed in said carrier matrix which substrate is detectably marked, e.g., dyed, and which substrate, upon action of a hydrolyzing enzyme thereon, is broken down into soluble fragments capable of diffusing through the carrier matrix to cause formation of an unmarked area in said detection layer; and measuring the size of the unmarked area as a measure of the activity of concentration of said enzyme.

3 Claims, 1 Drawing Figure

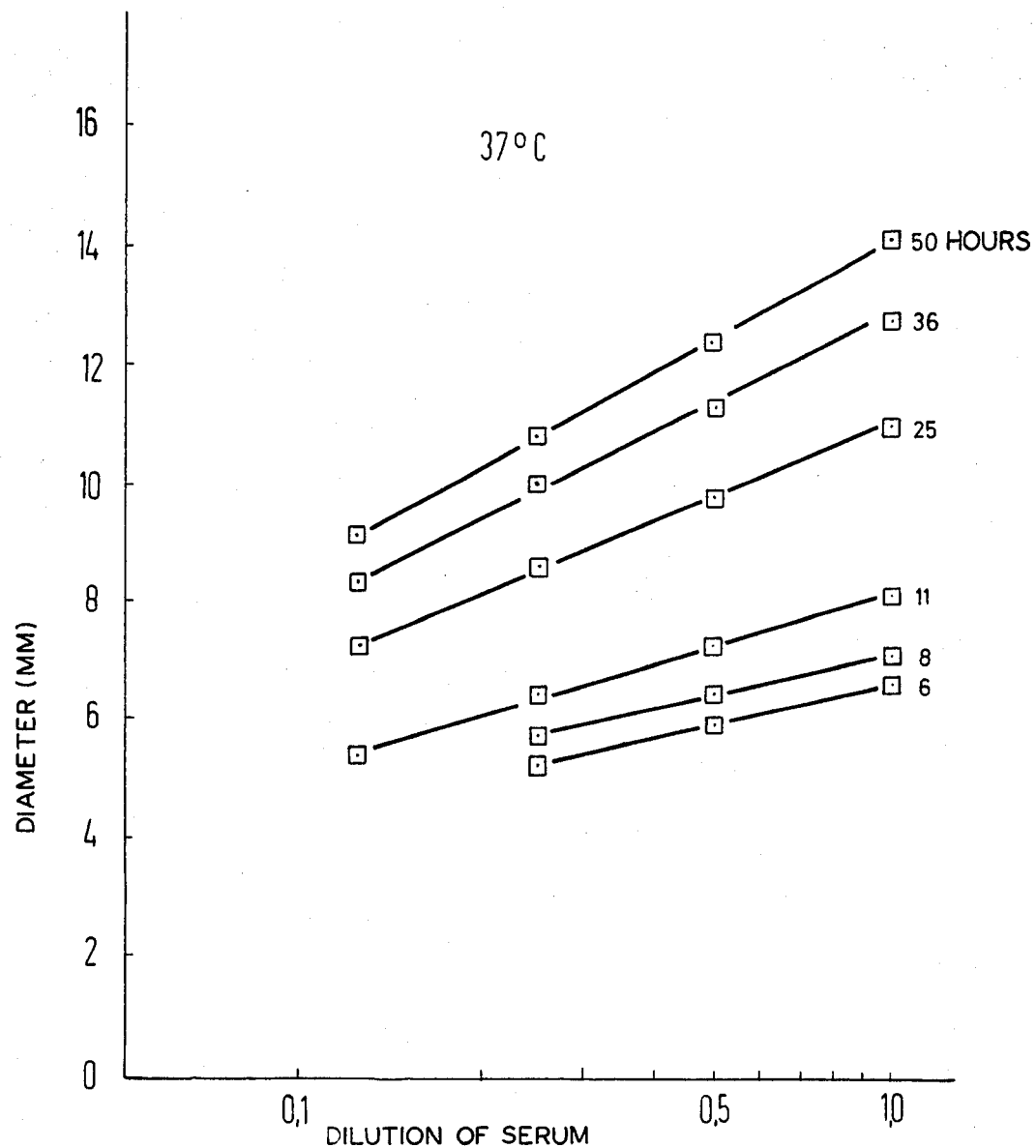

DETECTION OF HYDROLYZING ENZYMES

This application is a continuation of Ser. No. 178,671 filed Sept. 3, 1971, now abandoned.

The present invention relates to a composition and a simple, reliable method for the determination of the activity, or concentration, of hydrolyzing enzymes, especially, for instance, endo-enzymes which hydrolyze polysaccharides, proteins and various esters.

Various methods for the determination of hydrolyzing enzymes are known. All of these methods require however the use of a number of various reagents as well as pipetting procedures or the utilization of expensive apparatus or both. However, it is important in many cases to carry out a quick and reliable determination by a very simple method which can be carried out without any special auxiliary means; this is the case, for example, in the case of certain diseases or illnesses where a quick decision on the treatment to be taken is essential and this decision depends upon the determination of the activity of an enzyme, e.g., of amylase in the case of so-called "acute epigastrium".

Hence, there has been a need for a simple yet reliable method which does not require any special equipment and provides a quick and reliable determination of the aforementioned enzymes without the use of additional reagents and the like. This need has now been satisfied by the instant invention.

The method according to the invention for the determination of hydrolyzing enzymes comprises providing a substrate, rendered water-insoluble, in a carrier matrix, which is susceptible to being broken down by a solution of the hydrolyzing enzyme into fragments which are soluble and diffuse through the carrier matrix. The substrate is capable of being marked in such a manner that the presence of (marked) substrate can be detected optically or photographically and the unmarked area formed by the action of the enzyme in diffusing off the substrate is measured after a certain period of time. The invention can thus be simply carried out by applying a solution of the enzyme to a layer comprising the substrate in its matrix.

In the method according to the invention there is an exact ratio between the size of the unmarked area which is formed and the activity or concentration of the enzyme applied. This is surprising because diffusion can only start after splitting, i.e., breaking down, of the substrate and it could not be anticipated that both splitting rate and diffusion rate are related to one another in such a way that the size of the unmarked area or spot corresponds exactly to the activity of the enzyme.

As a carrier matrix for said carrier matrix/substrate layer there may be used agar gel, agarose gel, starch gel, quarane gelatin, polyacrylamide gel, silicate gel or other gel types or other material permitting diffusion such as e.g., cellulose, filter paper etc. Agar gel is preferred.

The substrate, which has to be present in the matrix in water-insoluble form, is marked with a dye, a radioactive substance or the like and then incorporated, e.g., mixed, into the matrix. The substrate is colored, e.g., by reaction with a dye and rendered insoluble to the matrix by, for example, cross-linking. Application of the enzyme then splits the insoluble substrate in soluble fragments which diffuse off through the carrier matrix. In this manner a decolorized, spot-like area is produced in the layer, the size of which is directly related to the activity or concentration of the enzyme. Since the enzyme solution can be applied simply in the form of a drop, after a certain period of time a round spot forms, the diameter of which can be simply measured and is directly proportional to the activity of the enzyme.

Hence, in the method according to the invention, a reaction takes place between the enzyme and the (previously made insoluble) substrate releasing soluble, marked fragments of the substrate containing the detectable color-producing groups or atoms. The fragments separate from the as yet undecomposed substrate, by diffusion within the carrier matrix, and as soon as the entire insoluble substrate is decomposed in a particular spot, this spot is completely decolorized.

The substrate used to carry out the invention is either an inherently water-insoluble and dyed substance, which is then mixed, e.g., with warm agar solution to prepare the layer composition, or is rendered water-insoluble by chemical linkage to an insoluble carrier, which is then in turn mixed with the carrier matrix, for example warm agar solution. The desired layer can be formed into a layer by simply applying it onto a suitable support, for instance a glass or plastic slab, a transparent or opaque sheet.

Thus, the substrate consists of a water-insoluble, marked (e.g., dyed or radioactively treated) and enzymatically decomposable network of molecules, for instance of the polysaccharide or protein type, these molecules being rendered insoluble by cross-linking unless they are inherently insoluble. It is also possible to chemically bind the soluble substrate to an inert and water-insoluble carrier, such chemical bonds being then broken by action of the enzyme.

The insoluble substrate may be prepared in various ways. It is for instance possible to link water-soluble polysaccharides or proteins or derivatives thereof, which can be hydrolyzed by endro-hydrolases, together to a three-dimensional, covalently linked network by means of bifunctional brigde forming agents or cross-linking agents. Subsequently the detectible, e.g., color-containing, groups or atoms can again be linked to the network, for example by forming covalent groups. Conversely it is also possible to first link the determinable groups or atoms to the soluble substrate molecules by covalent bonds and then carry out cross-linking. And finally, it is possible to achieve cross-linking and introduction of the detectible groups simultaneously.

Numerous types of substances are suitable as cross-linking agents. It is merely necessary that they are bifunctional and carry functions which can react with the substrate by forming a bond. Examples of such bridge-forming agents or cross-linking agents are the epoxides, the corresponding halo-hydrins, the isocyanates and the thioisocyanates. Such cross-linking agents can for instance react with hydroxyl groups or amino groups in the polysaccharides or in the protein or a derivative thereof, achieving the desired cross-linking and insolubility.

If the substrate is already water-insoluble per se, only the optically or photographically analyzable group has to be linked to the substrate.

Examples for optically or photographically analyzable "marking groups" are dyed groups or substances, fluorescent groups, radioactive groups and the like. Dyed groups are preferred since in that case it is very easy to make the measurement by simply measuring the diameter of the formed spot by means of a scale. The determination is almost as simple in the case of radioactively marked groups by placing a sheet which shows radioactive radiation, directly or following development, on the layer.

The introduction of the marking groups into the substrate can be carried out simply by reacting the substrate with hydroxyl groups or amino groups or other reactive groups in the polysaccharides and proteins or their derivatives. Suitable colorevolving groups are for instance those trademarked "Cibacron Scarlet 2G", "Procin Scarlet H 3G S", "Cibacron Blue 3G", "Procin Clue HBS", "Remazo Brilliant Blue", and the like, and available from Ciba A.G., Basel, Switzerland; Imperial Chemical Industries, England, and Farbwerke Hoechst A.G., Germany.

The introduction of fluorescent groups may for instance be achieved with fluorescent derivatives such as fluorescein isothiocyanate and other fluorescent compounds. If, for example, the activity of a proteolytic enzyme such as trypsin is to be determined, arginin-$\beta$-napthyl amine can be coupled with an insoluble carrier such as e.g., particulate dextran ("Sephadex") or another inert and water-insoluble material, which may be used as the substrate, and, following the action of trypsin, naphtyl amine is released which is fluorescent and can therefore be readily detected.

If the substrate is water-soluble, it can be linked to, for instance, activated dextran particles, activated cellulose particles, activated plastic particles, e.g., polystyrene particles, activated glass particles and the like, which are in turn mixed with the actual carrier matrix, for instance the agar, and transformed into a homogeneous layer.

Radioactive groups can also be introduced by many different techniques. It is for instance possible to introduce a group containing a radioactive iodine isotope, e.g. $I^{125}$. It is also possible to first introduce a group which does not contain an isotope and then, subsequently, incorporate a radioactive isotope into this group. In the case of polysaccharides, that may for instance be achieved by first introducing an allyl group, for example by means of allyl bromide, then adding a radioactive iodine isotope to the double bond. $I^{125}$ can be introduced into protein by several different techniques wherein the tyrosyl groups are iodinated. If the substrate does not contain any tyrosyl radicals, same may be introduced. Reactive groups particularly suitable for linking the marking group to the substrate are amino groups, hydroxyl groups and carboxyl groups. That may be realized by bridge linkage so that, for example, bonds of the following types result:

marking group — NH. CS. NH. — substrate
marking group — NH. CO. NH. — substrate
marking group — N = N — substrate The extent to which marking groups are introduced depends on the amount of such groups with which a sufficient determination is warranted. It should however be borne in mind not to introduce marking groups to such an extent that the reaction between the enzyme to be determined and the substrate is affected. It is within the skill of the artisan to determine this range, for a specific case.

If the water-insoluble substrate is required in the form of particles, it may be obtained by, for instance, grinding to the desired particle size. It is also possible to synthesize the substrate, for example by bubble polymerization, by emulsifying the reaction mixture in an inert liquid.

Of special importance regarding the process according to the invention is the surprising fact that the fragments formed upon action of the enzyme on the insoluble substrate diffuse into the carrier matrix in such a way that a sharp boundary results between hydrolyzed and non-hydrolyzed substrate so that a simple determination of the size of the hydrolyzed area is in effect possible by measuring its diameter, its surface area or the volume. The activity of the enzyme to be measured is of course influenced by the pH-value, temperature, substrate concentration, nature of the carrier matrix, its thickness and concentration. Under specific conditions set forth therefor it is however possible to readily carry out a quantitative determination in the simplest manner since the enzyme diffuses through the matrix rather slowly and it is not even necessary to inactivate the enzyme before measuring the size of the hydrolyzed spot. But it is also possible to destroy the enzyme activity by adding acids, alkalis, solvents, inhibitors, changing the temperature and the like, before such measurement.

A special advantage of the method according to the invention resides in that it can be easily carried out by simple means without any special equipment. A suitable medium according to the invention is a carrier coated with (a) a layer consisting of substrate rendered insoluble and marked in such a way that its presence can be detected optically or photographically and (b) a carrier matrix permitting the diffusion of the substrate fragments produced during enzymatic break-down or splitting. As a carrier medium for the invention a transparent or non-transparent slab or sheet may be used. Suitable materials are plastic, glass, metal and the like. Such media may be used by the physician for example to directly determine the enzyme activity of the patient by simply applying a drop of body fluid, in which the enzyme activity is to be determined, onto a small slab of the above-described coated carrier and measuring the diameter of the decolorized spot after a pre-determined period of time. Surprisingly it was found that enzymes can be determined in this manner with an error of less that 5%.

It is also possible to carry out the determination within a particularly short period of time by applying an electrical potential gradient to the medium in fashion similar to the procedure in electrophoresis, ellipsoidal areas being formed within a short period of time whose size or volume corresponds to the enzymatic activity under otherwise pre-determined conditions.

The following examples are illustrative of the invention but are not to be construed as limitative thereof.

EXAMPLE 1 — DETERMINATION OF α-AMYLASE

A 1% solution of agar in 20 millimole of sodium phosphate buffer pH 7.5 was prepared by heating the mixture to approx. 95° C. Then a starch polymer substrate dyed blue, as described in *Experientia* 25, page 555, was added while vigorously agitating the hot agar solution until a 0.5% suspension was obtained. The agar-substrate mixture obtained in this manner was applied onto a clean microscope carrier plate of a thickness of approx. 1 mm and allowed to solidify.

Onto the small plates prepared in this fashion 5 microliters of a urine sample were applied and the resulting specimen was allowed to stand at room temperature. Under the conditions as set forth the diameter of the decolorized spot was proportional to the enzyme activity in the specimen after only about one hour. The diameter continually increased in a directly linear manner with continuing incubation during at least 48 hours and allowed the determination of the activity at any time (with merely knowledge of the duration of the entire incubation period being required).

The above method was repeated as described, but 50 microliters of urine were used. After an incubation of only 15 minutes the activity of the α-amylase could be determined with an accuracy of approx. 95% by determining the diameter of the area turned colorless.

In the above example the agar may be replaced by agarose, pectin, gelatin, starch, quarane, polyacrylamide or silica gel without detriment to the determination.

The table below shows the dependence between the size of the decolorized area and the duration of the reaction under pre-determined conditions. The plates prepared as described above were used. The enzyme applied was 5 micrograms of α-amylase, obtained from *bacillus subtilis,* dissolved in 5 microliters of buffer. The incubation temperature was 37° C.

Table 1

| Duration of Incubation hrs. | Decolorized Area mm² |
|---|---|
| 2 | 70 |
| 6 | 173 |
| 10 | 280 |
| 20 | 543 |

Using human serum, dilution experiments were carried out. The serum was diluted by the factor of 0.125, 0.25, 0.5 and 1.0, applied onto test plates prepared as described above and incubated at 37° C. The diameters of the decolorized areas obtained are shown for different incubation periods in the attached drawing which is a plot of degree of dilution against decolorized spot diameter. The values obtained show that measurement of the diameter permits direct determination of the α-amylase activity.

EXAMPLE 2

As described in example 1, test plates were prepared using 1% agar solution as well as a dextran as substrate rendered insoluble by cross-linking with diepoxide and coupled with a blue dye.

The plates obtained in this manner were used to determine crude dextranase from *penicillium funiculosum* NRRL 1768. 5 Microliters of dextranase solution having an enzyme content of 125 micrograms were applied. The incubation temperature was 37° C, the pH value of the reagent medium was 5.5. The table below sets forth the size of the decolorized spots at various reaction times.

Table 2

| Reaction Time hrs. | Decolorized Area mm² |
|---|---|
| 2 | 105 |
| 4 | 174 |
| 8 | 299 |
| 25 | 799 |

A number of other test plates was incubated with 5 microliters each of dextranase solution having various dextranase contents. The temperature was 37° C, the reaction time 25 hours. The results obtained are listed in Table 3, below.

Table 3

| Microgram Dextranase | Decolorized Area mm² |
|---|---|
| 0.035 | 434 |
| 0.067 | 564 |
| 0.125 | 799 |
| 0.250 | 984 |

Table 3-continued

| Microgram Dextranase | Decolorized Area mm² |
|---|---|
| 0.500 | 1176 |
| 1.000 | 1389 |

EXAMPLE 3

As described in Example 1, test plates were prepared; as substrate an albumin was used rendered insoluble by cross-linking with diepoxide and dyed by the method described above.

5 microliters of a solution containing 0.5 micrograms of papain having an activity of 15 U/mg were pipetted onto a test plate obtained in this manner. The pH-value of the medium was 11.0, the incubation temperature 50° C. In addition the medium contained 0.5 M cysteine as an activator. Table 4 below shows the size of the decolorized area as a function of the duration of incubation.

Table 4

| Reaction Time hrs. | Decolorized Area mm² |
|---|---|
| 2 | 103 |
| 5 | 151 |
| 7 | 200 |
| 10 | 250 |

As described above, papain was applied onto test plates. The papain quantity varied between 0.5 and 30.0 micrograms of protein for each 5 microliters. Under the conditions set forth above, the values listed in Table 5 below were obtained after 5 hours.

Table 5

| Papain μg | Decolorized Area mm² |
|---|---|
| 0.5 | 151 |
| 2.5 | 236 |
| 10.0 | 324 |
| 30.0 | 385 |

It will be understood that the specification and examples are illustrative but not limitative of the present invention and that other embodiments within the spirit and scope of the invention will suggest themselves to those skilled in the art.

What is claimed is:

1. Method for the detection of the activity, or concentration, of a hydrolyzing enzyme selected from the group consisting of alpha-amylase, dextranase, and papain, which method comprises applying a solution of said hydrolyzing enzyme onto a detection layer consisting essentially of a carrier matrix gel inert to the enzyme and permitting diffusion of substrate fragments therein and, dispersed throughout said matrix gel, a dyed intermolecularly cross-linked substrate selected from the group consisting of starch, dextran, cellulose and albumin, cross-linked with a diepoxide to render the substrate insoluble in the matrix gel, and measuring the size of an unmarked area formed in said gel due to fragmentation and diffusion of the dyed substrate by action of the enzyme thereon, as a measure of the amount of concentration of said enzyme.

2. Method as claimed in claim 1 wherein said matrix gel is an agar or a starch gel.

3. Method as claimed in claim 1 wherein the time required for producing the unmarked area after complete action of the enzyme on the substrate is first determined for a specific enzyme/detection layer combination under specific conditions and said hydrolyzing enzyme is then determined by measuring said unmarked area after a predetermined time shorter than the first determined time and comparing the unmarked area with a reference standard to calculate the amount, or concentration, of said hydrolyzing enzyme.

* * * * *

UNITED STATES PATENT AND TRADEMARK OFFICE
CERTIFICATE OF CORRECTION

PATENT NO. : 4,066,509
DATED : January 3, 1978
INVENTOR(S) : Miroslav Ceska

It is certified that error appears in the above-identified patent and that said Letters Patent are hereby corrected as shown below:

Title page, German priority missing, should read:
                    June 15, 1971, Germany...P2129661.7
Title page, Abstract, last line, "of" second occurrence
                    should read -- or --.
Col. 3, l. 10, "Clue" should read -- Blue " --.
Col. 6, l. 55, "of" second occurrence should read -- or --.

Signed and Sealed this

First Day of May 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,066,509
DATED : January 3, 1978
INVENTOR(S) : Miroslav Ceska

It is certified that error appears in the above-identified patent and that said Letters Patent are hereby corrected as shown below:

On the title page the following should be added:

-- [30] Foreign Application Priority Data

June 15, 1971    Germany ............P2129661.7 --.

Signed and Sealed this

Twenty-second Day of May 1979

[SEAL]

Attest:

RUTH C. MASON
*Attesting Officer*

DONALD W. BANNER
*Commissioner of Patents and Trademarks*